(12) United States Patent
Gregg et al.

(10) Patent No.: US 8,778,020 B2
(45) Date of Patent: Jul. 15, 2014

(54) REPLACEMENT HEART VALVE LEAFLET STITCHING METHOD AND DEVICE

(71) Applicant: Boston Scientific Scimed, Inc., Maple Grove, MN (US)

(72) Inventors: Peter W. Gregg, Santa Cruz, CA (US); Daniel K. Hildebrand, San Francisco, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 5 days.

(21) Appl. No.: 13/671,796

(22) Filed: Nov. 8, 2012

(65) Prior Publication Data

US 2013/0116778 A1  May 9, 2013

Related U.S. Application Data

(60) Provisional application No. 61/557,201, filed on Nov. 8, 2011.

(51) Int. Cl.
 *A61F 2/24* (2006.01)
(52) U.S. Cl.
 CPC ............ *A61F 2/24* (2013.01); *A61F 2220/0075* (2013.01); *A61F 2/2415* (2013.01)
 USPC ........................................................ 623/2.13
(58) Field of Classification Search
 USPC .......................................... 623/2.1, 2.12–2.19
 See application file for complete search history.

(56) References Cited

U.S. PATENT DOCUMENTS

| | | | |
|---|---|---|---|
| 5,411,552 A | 5/1995 | Andersen et al. | |
| 6,168,614 B1 | 1/2001 | Andersen et al. | |
| 6,682,559 B2 | 1/2004 | Myers et al. | |
| 7,137,184 B2 | 11/2006 | Schreck | |
| 7,329,279 B2 | 2/2008 | Haug et al. | |
| 7,563,280 B2 | 7/2009 | Anderson et al. | |
| 2005/0143809 A1 | 6/2005 | Salahieh et al. | |
| 2006/0206202 A1 | 9/2006 | Bonhoeffer et al. | |
| 2007/0250163 A1 | 10/2007 | Cassani | |
| 2010/0023120 A1* | 1/2010 | Holecek et al. | ............. 623/2.19 |
| 2010/0185277 A1 | 7/2010 | Braido et al. | |

FOREIGN PATENT DOCUMENTS

| | | |
|---|---|---|
| DE | 202004009070 | 8/2004 |
| WO | 9843556 | 10/1998 |
| WO | 0048531 | 8/2000 |

OTHER PUBLICATIONS

U.S. Appl. No. 61/544,487, filed on Oct. 7, 2011.
PCT Search Report and Written Opinion for PCT/US12/64126.

* cited by examiner

*Primary Examiner* — Thomas J Sweet
*Assistant Examiner* — Matthew Schall
(74) *Attorney, Agent, or Firm* — Vidas, Arrett & Steinkraus, P.A.

(57) ABSTRACT

A replacement heart valve and stitching method for reducing the unexpanded profile of the replacement heart valve are herein provided. The method includes whip stitching a plurality of leaflets together with a first whip stitch pattern a second whip stitch pattern which overlaps the first whip stitch pattern and is wound in an opposite direction. The method further involves securing the valve leaflets to one another via a running stitch.

13 Claims, 12 Drawing Sheets

REPLACEMENT HEART VALVE LEAFLET STITCHING METHOD AND DEVICE

CROSS-REFERENCE TO RELATED APPLICATIONS

This Application claims priority to U.S. Provisional Application No. 61/557,201, filed Nov. 8, 2011, the entire contents of which are herein incorporated by reference.

STATEMENT REGARDING FEDERALLY SPONSORED RESEARCH

Not Applicable

BACKGROUND OF THE INVENTION

Various procedures for fixing or replacing defective heart valves are known in the art. Some examples of replacement valves and procedures are shown, for example, in U.S. Pat. No. 7,329,279 and US Publication Number 2005/0143809, which are herein incorporated by reference.

Types of percutaneously implanted replacement heart valves are inserted via a catheter. Upon deployment from the catheter, the replacement heart valve is expanded. While inside the catheter, however, it is desirable for the replacement heart valve to take on a reduced profile. Additionally, it is desirable for that reduced profile to be as reasonably small as is possible. The larger the profile of the replacement hear valve, the larger the catheter that will be required to house the replacement heart valve. Further, a smaller profile catheter helps to minimize the risk of damage to the body lumen through which the catheter is inserted.

Consequently, there remains a need for a replacement heart valve that has a reduced profile when in an unexpanded configuration. Additionally, the reduced profile replacement heart valve must retain the requisite strength to expand and reliably function.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In some embodiments, a method of forming a replacement heart valve comprises providing a plurality of valve leaflets each having a side edge, positioning two of the valve leaflets in facing orientation such that the side edges are aligned, providing a first thread of suture material, and threading the valve leaflets together. In some embodiments, the method further comprises threading the first thread of suture material through the two valve leaflets in a first pattern of whip stitches. And, in some embodiments, the method comprises threading the first thread of suture material through the two valve leaflets in a second pattern of whip stitches. In some embodiments, the first pattern of whip stitches is threaded in a first direction and the second pattern of whip stitches is threaded in a second direction opposite the first direction. In some embodiments, the method comprises providing a second thread of suture material. The method further comprises threading the second thread of suture material through the two valve leaflets in a first running stitch, the first running stitch being parallel to the side edges. In some embodiments, the method comprises threading the second thread of suture material through the two valve leaflets in a second running stitch. In some embodiments, the second running stitch is parallel to the side edges.

BRIEF DESCRIPTION OF THE SEVERAL VIEWS OF THE DRAWING(S)

FIGS. 5A-6H show the leaflets being assembled.

DETAILED DESCRIPTION OF THE INVENTION

While this invention may be embodied in many different forms, there are described in detail herein specific embodiments. This description is an exemplification of the principles of the invention and is not intended to limit it to the particular embodiments illustrated.

For the purposes of this disclosure, like reference numerals in the figures shall refer to like features unless otherwise indicated.

Figure 7:
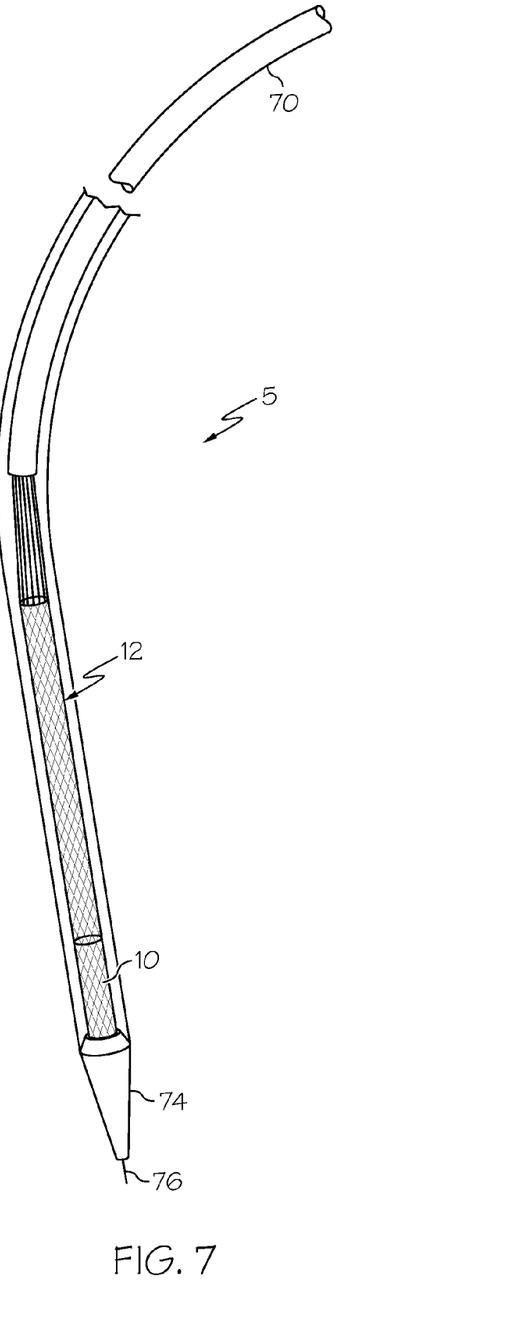
FIG. 7 shows a catheter, replacement heart valve, and anchor, the replacement heart valve and anchor being in an unexpanded configuration.

Construction of the replacement heart valve impacts the profile of the replacement heart valve in an unexpanded configuration, for example as shown in FIG. 7. The following description and drawings illustrate leaflet stitching method(s) and device(s) that, when reconfigured to an unexpanded configuration, reduce the profile of the replacement heart valve.

Figure 1:
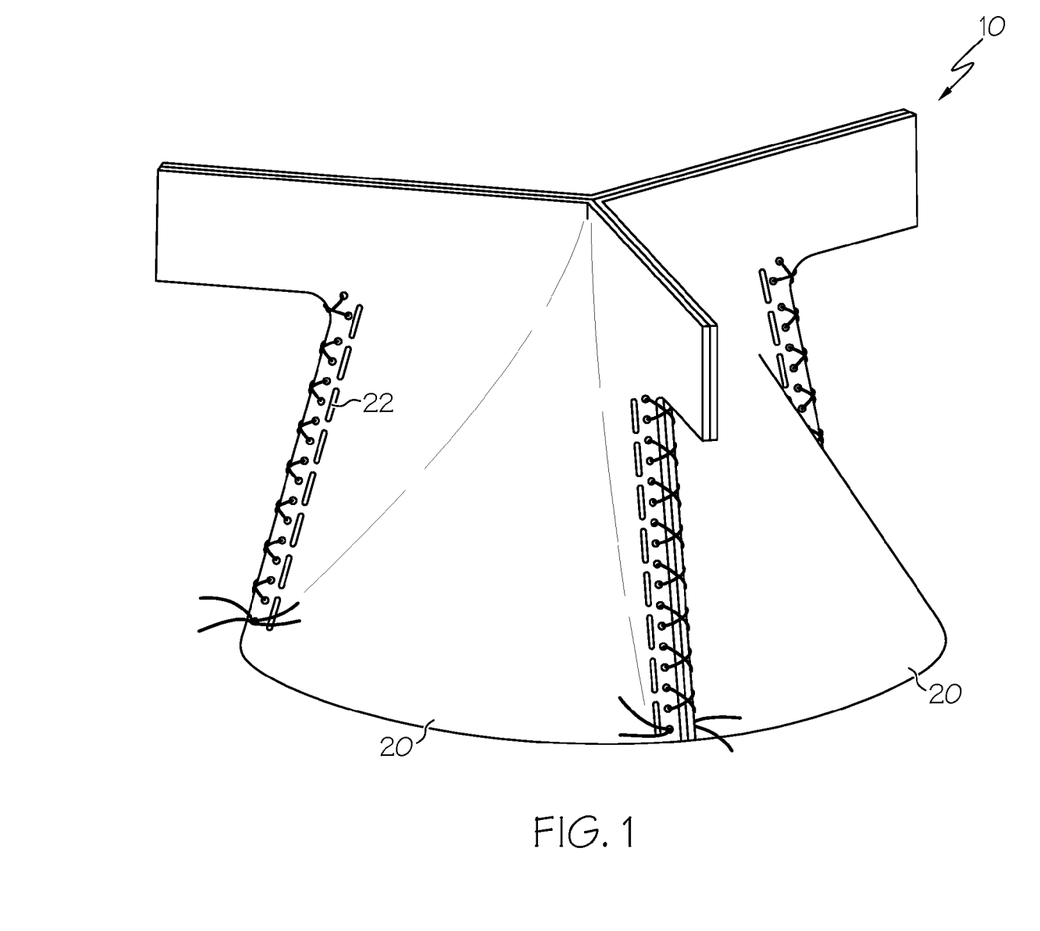
FIG. 1 shows a perspective view of an embodiment of a replacement heart valve.

Turning now to FIG. 1, in some embodiments, a replacement heart valve 10 comprises a plurality of leaflets 20. As further shown in FIG. 1, the replacement heart valve 10 has three leaflets 20; the replacement heart valve 10 can have any suitable number of leaflets 20, for example two, three, four, five, or more leaflets 20. In some embodiments, leaflets 20 are attached to one another via a plurality of sutures 22. In some embodiments, the sutures 22 are threaded through portions of the leaflets 20 in a particular fashion, as described herein, to help minimize the profile of the replacement heart valve 10 during percutaneous insertion.

Figure 2:
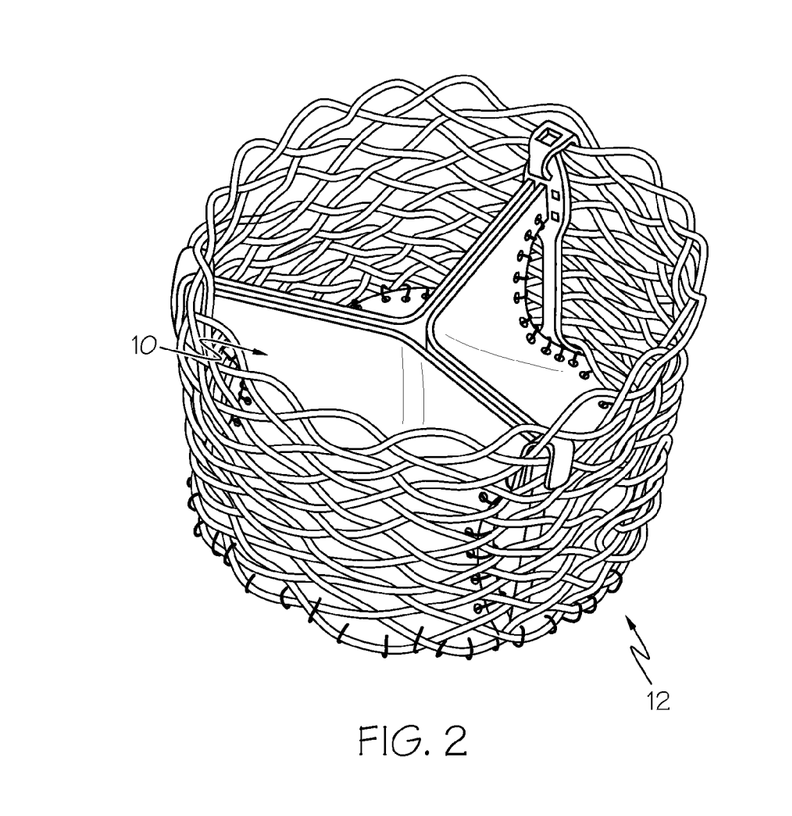
FIG. 2 shows a perspective view of an anchor and the embodiment of the replacement heart valve of FIG. 1.

Turning to FIG. 2, in some embodiments, the replacement heart valve 10 is attached to an anchor 12. In some embodiments, the anchor 12 comprises a braided wire, for example as disclosed in US Publication Number 2005/0143809, titled, "Methods and Apparatus for Endovascularly Replacing a Heart Valve," and filed on Nov. 5, 2004, which is herein incorporated by reference.

Figure 3:
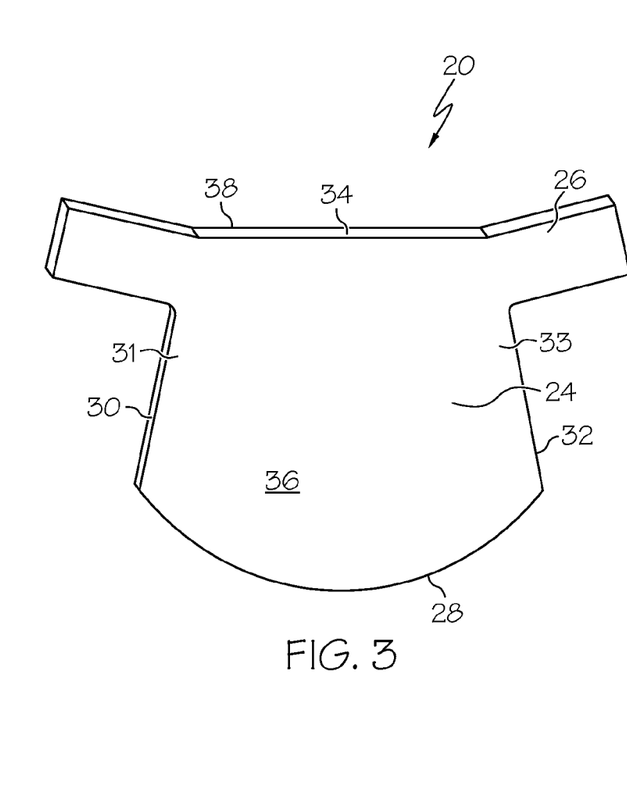
FIG. 3 shows a perspective view of an embodiment of a leaflet.

In some embodiments, for example as shown in FIG. 3, a leaflet 20 comprises a body portion 24 and sleeve portions 26. In some embodiments, the body portion 24 has a bottom edge 28, a first side edge 30, a second side edge 32, and a free edge 34. The leaflet 20 further comprises a front 36, a back 38, a first side 31, adjacent to the first side edge 30, and a second side 33, adjacent to the second side edge 32. In some embodiments, the front 36 of the leaflet 20 has a different texture than the back 38. In some embodiments, this occurs where the leaflet 20 is made from pig, cow, or other natural animal tissue. In some embodiments, the leaflet 20 is made from bovine pericardium. The leaflets 20 can also be made from a synthetic material.

Figure 4A:
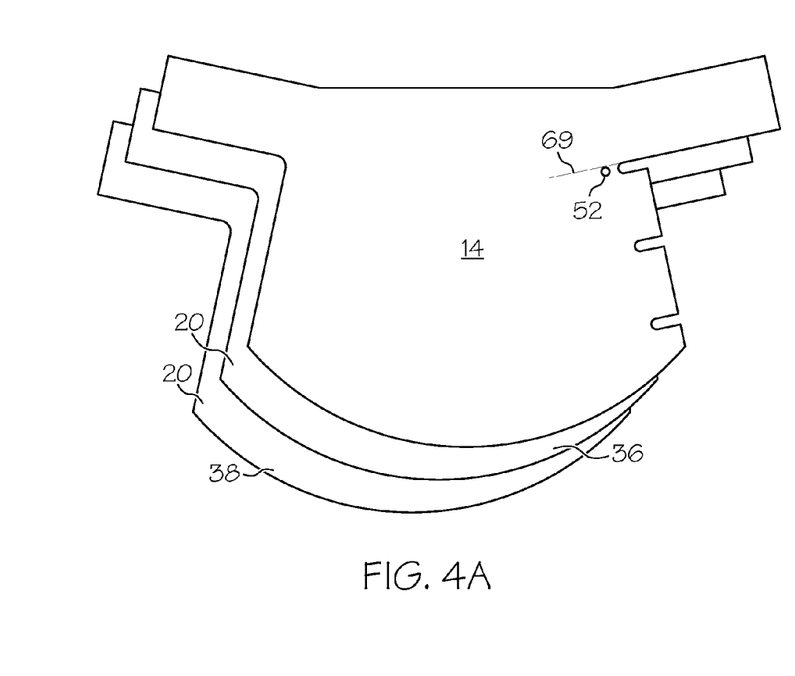
FIG. 4A shows an exploded view, including two leaflets and a fixture.

In some embodiments, the leaflets 20 are assembled by aligning two leaflets 20 with a fixture 14, for example as shown in the exploded view of FIG. 4A. The leaflets 20 are stacked, one on top of the other, and aligned with the fixture 14. Additionally, where the front 36 of the leaflet 20 has a different texture than the back 38, the desired texture is selected to face a particular direction. In some embodiments, for example where the leaflet 20 is formed from animal tissue, the leaflet 20 has a "fuzzy" side. Generally, where the leaflet 20 is made from bovine pericardium tissue, the tissue has a protective sack that surrounds the heart of the cow. One side of this tissue is fibrous, while the other side is relatively smooth. When used to form the leaflets 20, the "fuzzy" or fibrous side is assembled on the inflow side of the leaflets 20, the side of the leaflets 20 facing one another. This permits the leaflet to be washed during valve opening, reducing the risk of thrombus formation.

Figure 4B:
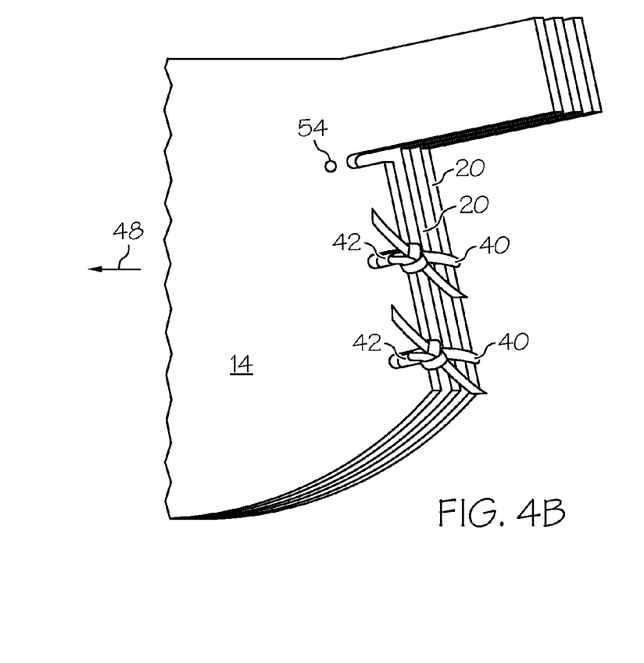
FIG. 4B shows a partial view of two leaflets and the fixture.

Once the leaflets 20 and the fixture 14 are aligned and stacked, temporary sutures 40 are threaded through one or more of the slots 42 on the fixture 14 and through a respective side, e.g., 31, 33, of the leaflets 20. As shown in FIG. 4B, the temporary sutures 40 are threaded through two of the slots 42, for example via a #15 needle (not shown). Further, in some embodiments, the temporary sutures 40 are formed of 5-0 cottony suture material. After being threaded through slots 42, the temporary sutures 40 are knotted and trimmed, as shown in FIG. 4B.

After the leaflets 20 are attached via temporary sutures 40, the fixture 14 is removed. The fixture 14 is detached from temporary sutures 40 by way of slots 42. Stated differently, in some embodiments, the fixture 14 is removed by sliding the fixture 14 in the direction of arrow 48. In this way, the temporary sutures 40 are able to be extracted from slots 42 while connecting the leaflets 20.

Figure 5A:
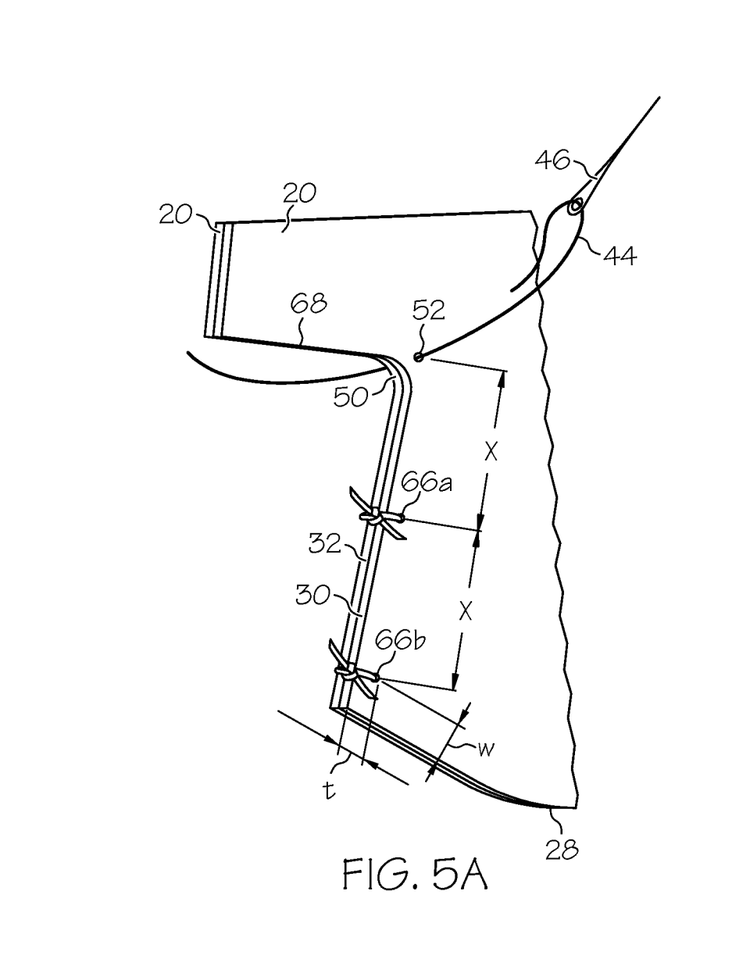

Turning to FIG. 5A, in some embodiments, the perforations 66a, 66b, through which the temporary sutures 40 are disposed, are a distance t from the respective side edge (30, 32). In some embodiments, the distance t is between 0.8 and 1.1 mm, and in some embodiments is 0.95 mm. Additionally, in some embodiments, the second perforation 66b is located a distance w from the bottom edge 28. In some embodiments, the distance w is between 0.2 and 1.0 mm. In some embodiments, the distance w is 0.3-0.8 mm. Moreover, the first perforation 66a is located adjacent the respective side edge (30, 32) a distance x from the second perforation 66b. In some embodiments, the first perforation 66a is located half way between the second perforation 66b and the line extending from the lower sleeve edge 68.

In some embodiments, once the leaflets 20 are aligned, stacked, and temporarily held together via temporary sutures 49, they are then ready to be permanently attached to one another. A first thread 44 of permanent suture material is provided and inserted through the eye of needle 46. The first thread 44 is then inserted through the leaflets 20 adjacent to armpit 50. In some embodiments, the initial insertion location 52 is marked via hole 54 through fixture 14 (FIG. 4B). In some embodiments, the first thread 44 is inserted through the hole 54 prior to removal of the fixture 14. In this instance, the fixture 14 is pulled over the first thread 44. In some embodiments, for example as shown in FIG. 4A, the top of the initial insertion location 52 is aligned with the lower sleeve edge 68, as depicted via extension line 69. Further, the initial insertion location 52 is aligned with the first and second perforations 66a, 66b.

Figure 5B:
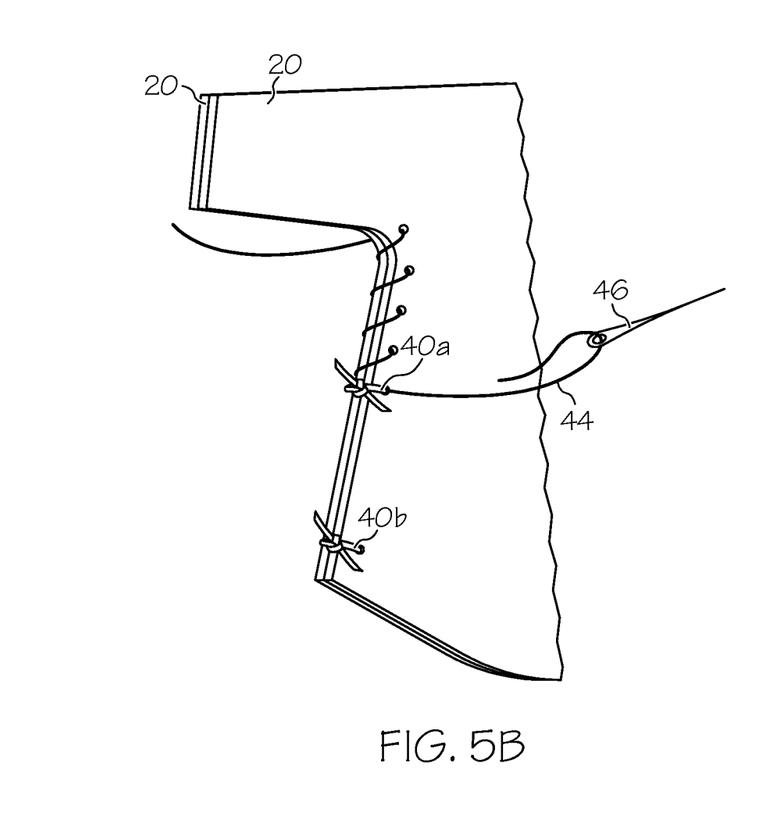

As shown in FIG. 5B, the first thread 44 is sewn through the leaflets 20 in a series of whip stitches. In some embodiments, there are four whip stitches between the initial insertion location 52 and the first temporary suture 40a.

Figure 5C:
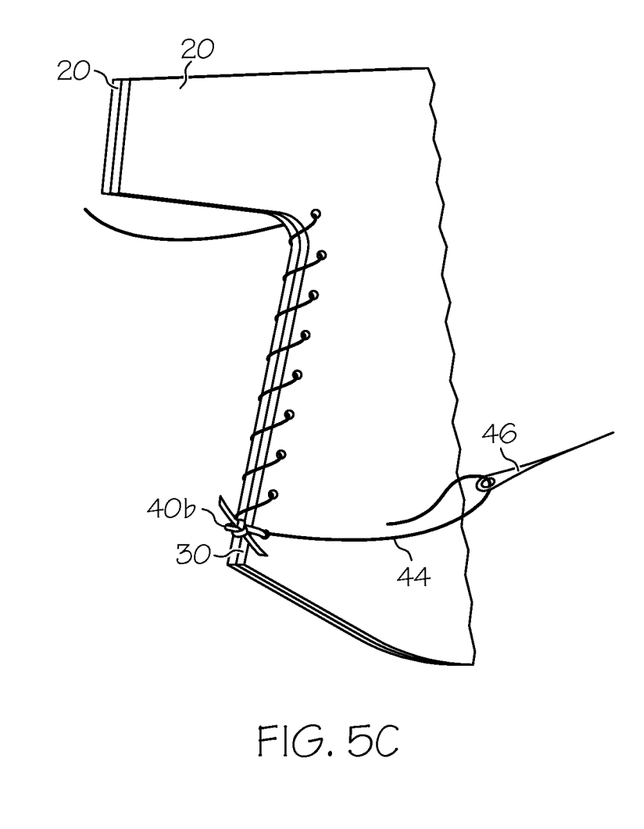

In some embodiments, the first temporary suture 40a is removed as the whip stitching approaches its location. Further, the hole used for temporary suture 40a is reused by removing the temporary suture 40a and inserting the first thread 44, for example as shown in FIGS. 5B and 5C. Reuse of the hole maintains the structural integrity of the leaflets 20. The whip stitching then continues until the second temporary suture 40b is reached, at which point it is removed and the first thread 44 is inserted through the hole previously occupied by the temporary suture 40b. In some embodiments, there are four whip stitches between the hole previously occupied by the first temporary suture 40a and the hole previously occupied by the second temporary suture 40b. Thus, in some embodiments, there are eight whip stitches along the length of the respective side edge (e.g., 30, 32).

Figure 5D:
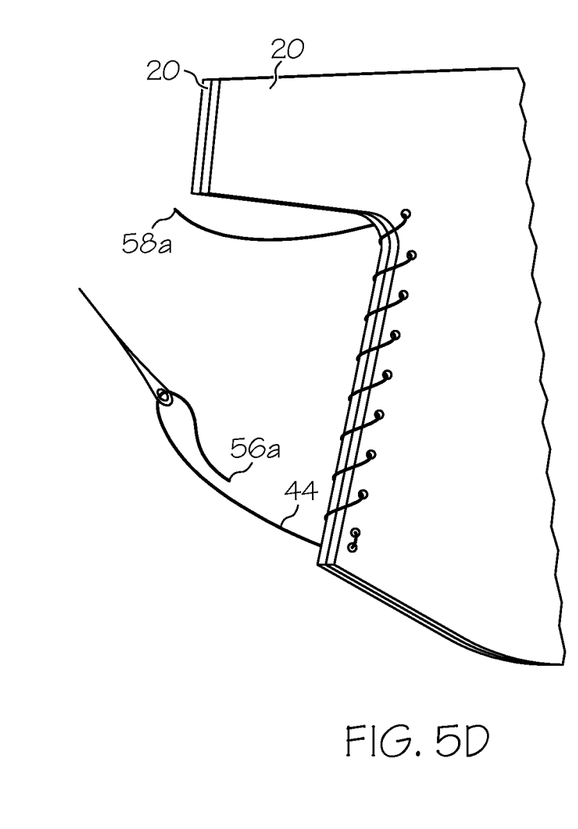
Figure 5E:
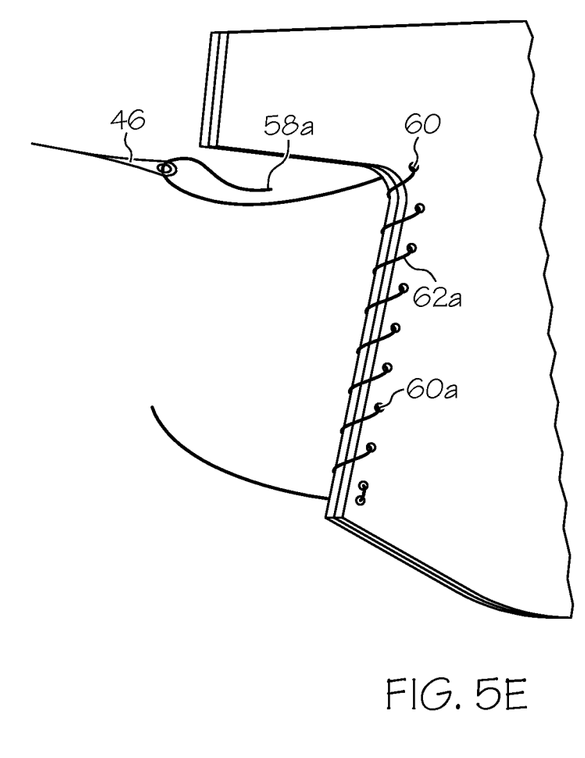
Figure 5F:
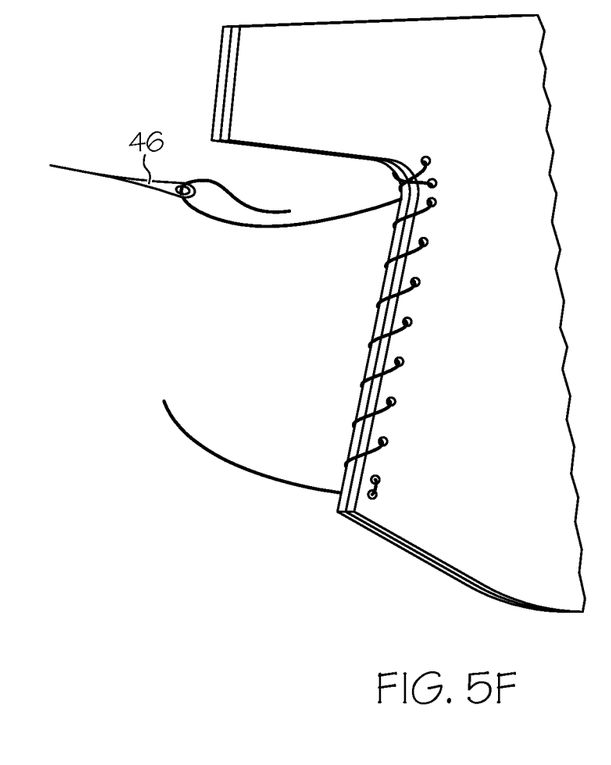
Figure 5G:
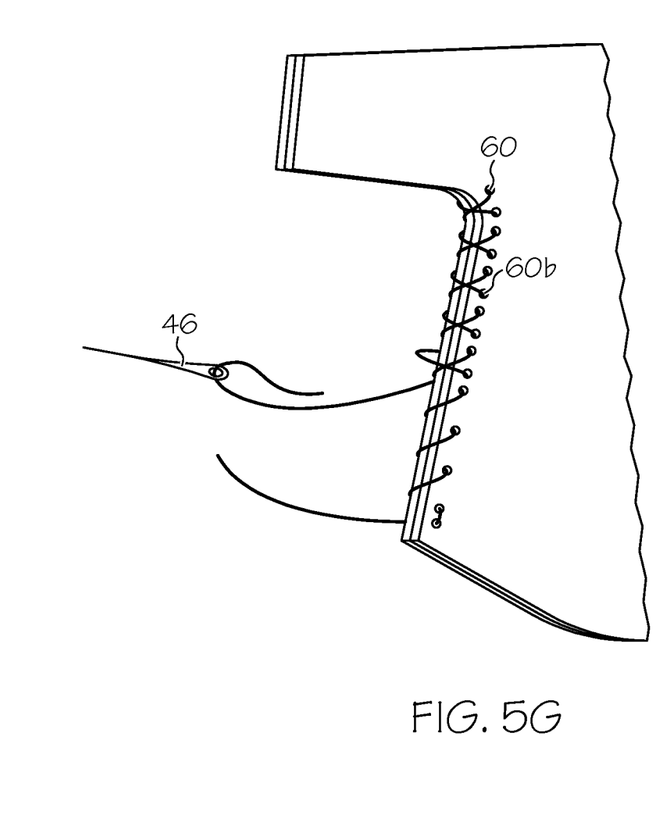

With reference to FIG. 5D, after the last whip stitch, the first thread 44 is threaded back through the leaflets 20 so that the leading end 56a of the first thread 44 and the trailing end 58a of the thread are on the same side of the leaflets 20.

Turning to FIGS. 5E-5H, in some embodiments, the needle 46 is relocated on the trailing end 58a of the first thread 44. Thereafter, the first thread 44 is threaded in a whip stitch pattern 62b (FIG. 5H) opposite the direction of the existing or first whip stitch pattern 62a. As shown, the new whip stitches of the second whip stitch pattern 62b overlap the existing whip stitches 62a; in some embodiments, the second whip stitch pattern 62b has eight whip stitches. Further, in some embodiments, the whip stitches are evenly spaced, with the spacing between stitching holes 60a being the same and the spacing between stitching holes 60b being the same. Moreover, in some embodiments, the spacing between adjacent stitching holes 60a and 60b is the same along the length of the whip stitch patterns.

Figure 5H:
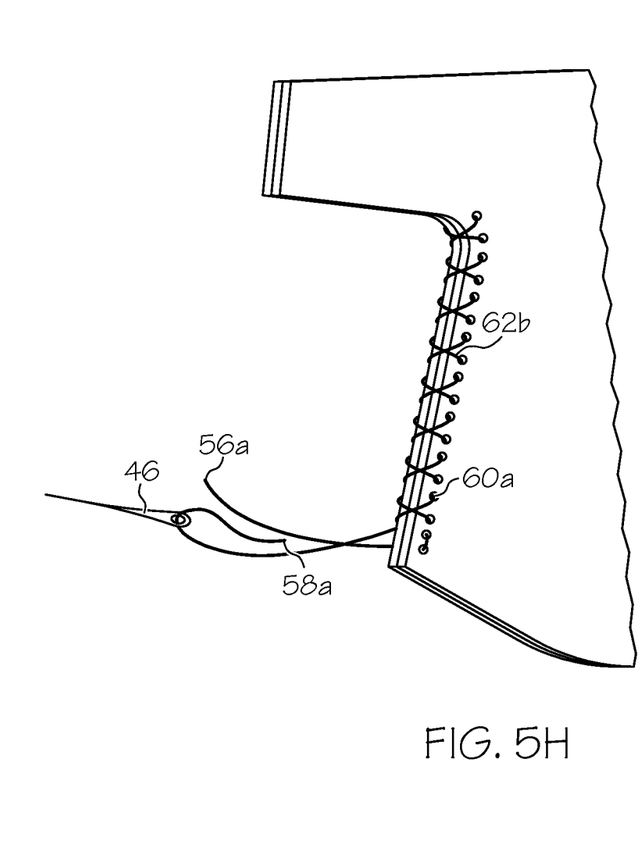

In some embodiments, after completion of the first and second whip stitch patterns 62a, 62b, the leading and trailing ends 56a, 58a are tied together. In some embodiments, the leading and trailing ends 56a, 58a are tied to one another via a slip knot followed by a square knot. Other methods of securing the ends are also suitable. For example, the ends can be tied in any combination of suitable knots, adhered together by heating or gluing. The leading and trailing ends 56a, 58a are trimmed to remove excess material. In some embodiments, they are trimmed between 1 and 2 mm from the knot.

Figure 6A:
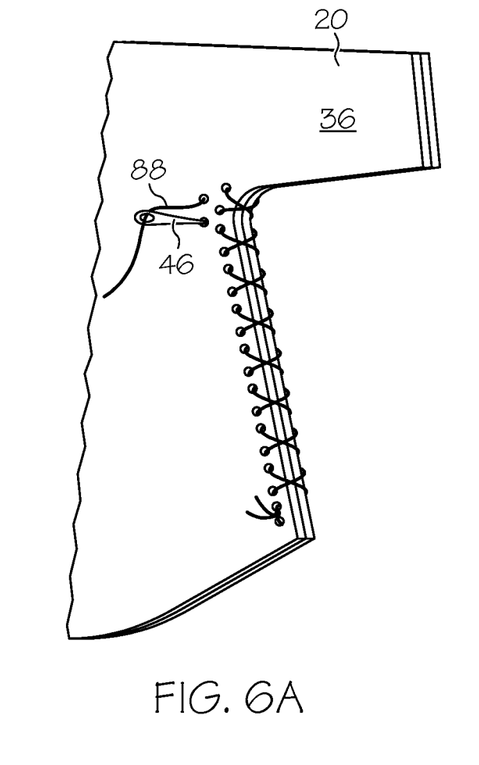
Figure 6B:
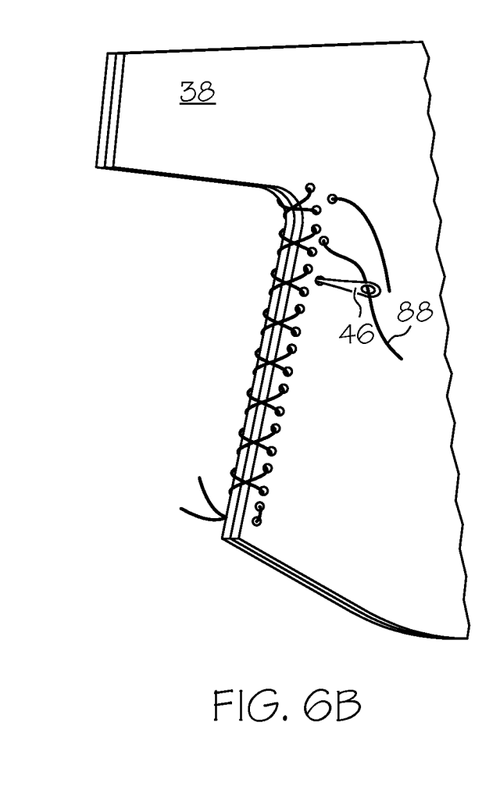
Figure 6C:
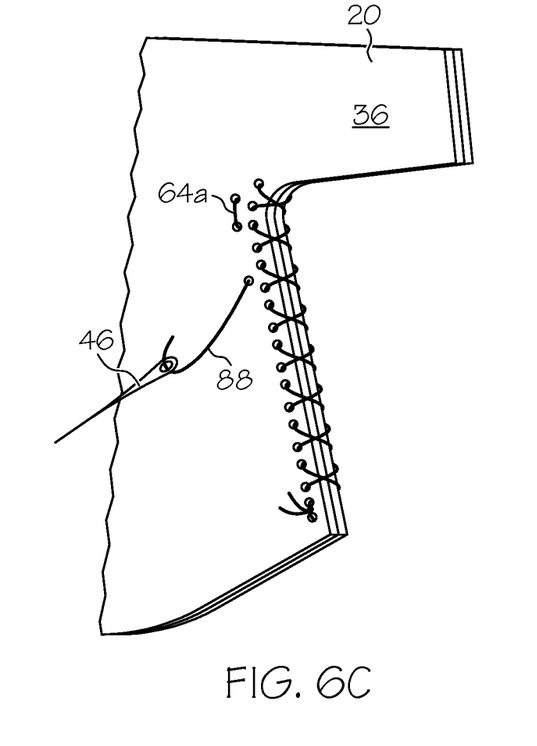
Figure 6D:
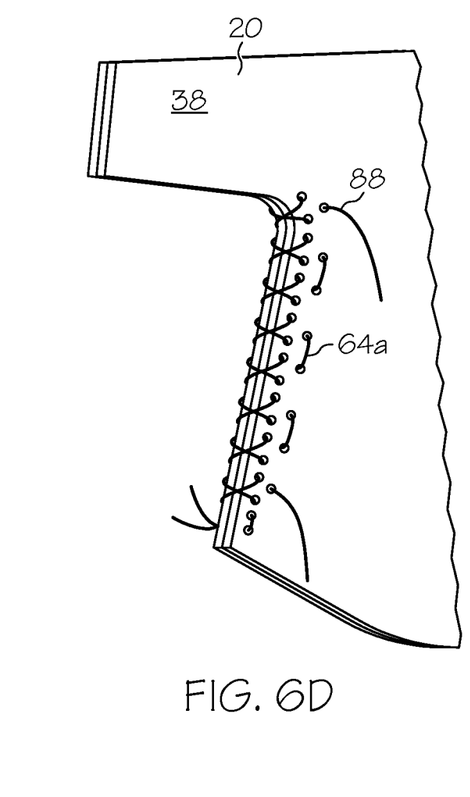
Figure 6E:
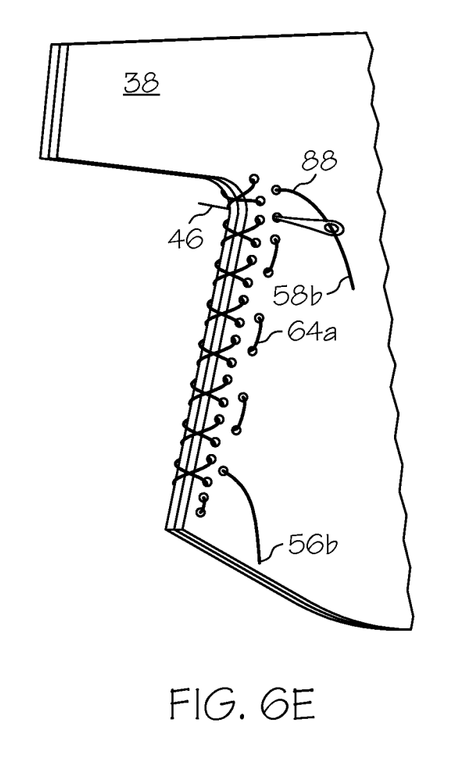
Figure 6F:
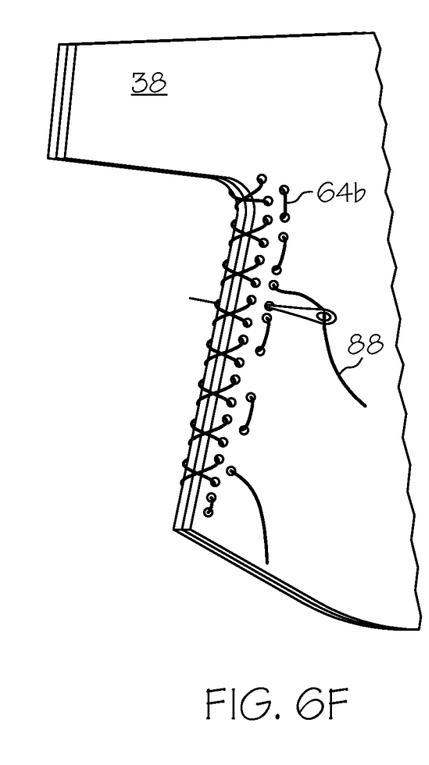

Turning to FIG. 6A, in some embodiments, a second thread 88 is threaded through the leaflets 20 adjacent to the first and second whip stitch patterns 62a, 62b. In some embodiments, the needle 46 is located at the approximate midpoint of the second thread 88 prior to stitching. Subsequently, in some embodiments, the second thread 88 is inserted through the leaflets 20 from the back 38 (FIG. 6B). As shown in FIGS. 6A-6D, the second thread 88 is stitched in a first running stitch 64a. In some embodiments, the first running stitch 64a is located between 0.1 and 0.5 mm from the first and second whip stitch patterns 62a, 62b. In some embodiments, the running stitch 64a is 0.3 mm from the first and second whip stitch patterns 62a, 62b. Further, in some embodiments the running stitch 64a has three stitches on the back 38 and four stitches on the front 36. At the end of the first running stitch 64a, a remainder of the second thread 88 extends from the back 38.

Figure 6G:
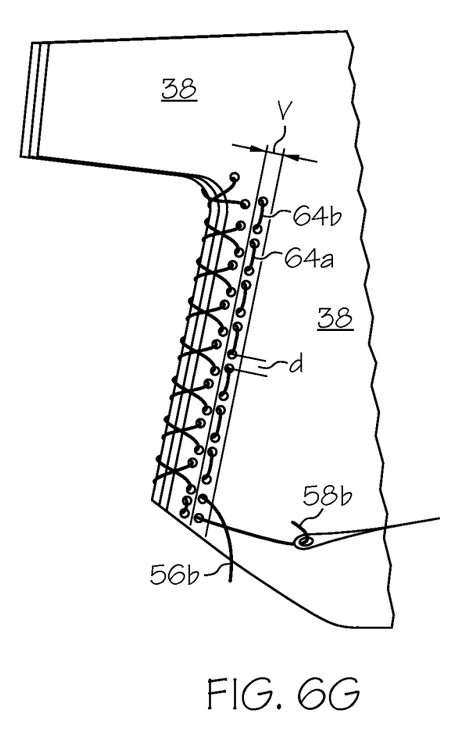
Figure 6H:
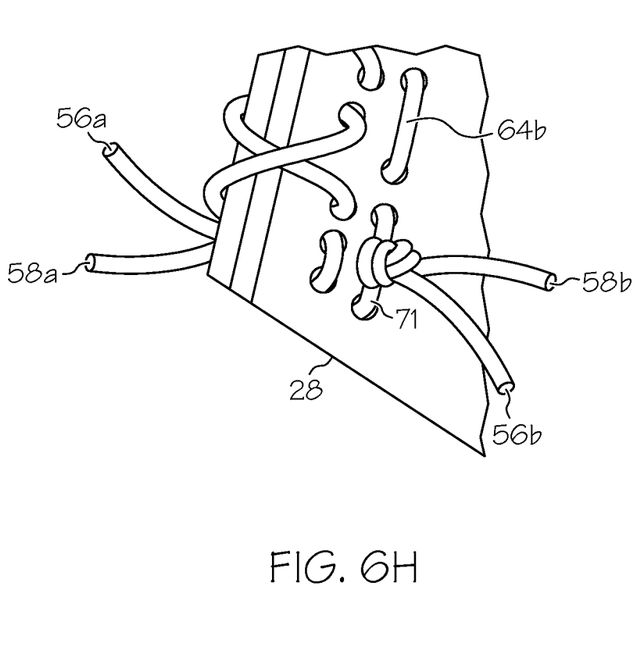

Turning to FIGS. 6E-6H, the needle 46 is relocated over the trailing end 58b in order to thread the remaining length of the second thread 88 through the leaflets 20, as shown. In particular, in some embodiments, the needle 46 and trailing end 58b are stitched to form a second running stitch 64b. In some embodiments, the stitches of the first running stitch 64a alternates with the stitches of the second running stitch 64b. As illustrated in FIG. 6G, in some embodiments, the distance, d, between adjacent stitches is between 0.1 and 0.3 mm and, in some embodiments, between 0.15 and 0.25 mm. In some embodiments, the running stitch 64b has four stitches on the back 38 and four stitches on the front 36 such that the leading end 56b and the trailing end 58b can be tied together on the same side (e.g., back 38). With reference to FIG. 6H, in some embodiments the leading end 56b and trailing end 58b are tied together via a slip knot followed by a square knot. The ends of the second thread 88 are trimmed between 1 and 2 mm from the knot. In addition to knotting, other suitable knots and methods, for example as discussed above, can also be employed. In some embodiments, the last stitch 71 between 0.2 and 1.0 mm from the bottom edge 28. In some embodiments, the last stitch 71 is between 0.3 and 0.8 mm from the bottom edge. 28.

In some embodiments, the first running stitch 64a and the second running stitch 64b are offset, within a range, v, as shown in FIG. 6G. In some embodiments, the range, v, is less than 0.3 mm.

Returning to FIG. 1, the replacement heart valve 10 can further be assembled by repeating the above-described process for the intersection of each leaflet 20. Moreover, subsequent to formation of the heart valve 10, it can be combined with anchor 12 to form an implantable valve assembly.

Turning to FIG. 7, the replacement heart valve 10 and anchor 12 are shown in a reduced profile, for example as retained in catheter 70 for insertion into the patient's body. Moreover, in some embodiments, the catheter assembly 5 comprises a nosecone 74 and a guide wire 76 extending through the catheter assembly 5. Further detail of a suitable catheter assembly is shown in PCT WO2005/062980, titled "Repositionable Heart Valve," with an international filing date of Dec. 22, 2004, which is herein incorporated by reference.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

What is claimed is:

1. A method of forming a replacement heart valve, the method comprising:
   providing a plurality of valve leaflets, each leaflet having a side edge;
   positioning two of the valve leaflets in facing orientation such that side edges of the leaflets are aligned;
   providing a first thread of suture material;
   threading the first thread of suture material through the two valve leaflets in a first pattern of whip stitches;
   threading the first thread of suture material through the two valve leaflets in a second pattern of whip stitches, wherein the first pattern of whip stitches is threaded in a first direction and the second pattern of whip stitches is threaded in a second direction opposite the first direction;
   providing a second thread of suture material;
   threading the second thread of suture material through the two valve leaflets in a first running stitch, the first running stitch being parallel to the side edges; and
   threading the second thread of suture material through the two valve leaflets in a second running stitch, the second running stitch being parallel to the side edges.

2. The method of claim 1, wherein the plurality of valve leaflets further comprises a third valve leaflet, and the method of forming a replacement heart valve further comprises positioning the third valve leaflet in facing orientation with the two valve leaflets such that side edges of the three valve leaflets are aligned with one another to form a tri-leaflet valve.

3. The method of claim 2, wherein each leaflet comprises a first side edge and a second side edge, the first side edge of a first leaflet being attached to a second side edge of the third leaflet, the second side edge of the first leaflet being attached to the first side edge of the second leaflet, and the second side edge of the second leaflet being attached to the first side edge of the third leaflet.

4. The method of claim 2, wherein the replacement heart valve is attached to an expandable anchor.

5. The method of claim 1, wherein the step of positioning two of the valve leaflets comprises aligning the leaflets with a fixture.

6. The method of claim 5, wherein the fixture defines a plurality of slots along an edge thereof.

7. The method of claim 6 further comprising inserting temporary sutures through the slots and leaflets.

8. The method of claim 7 further comprising removing the fixture and the temporary sutures.

9. The method of claim 5, wherein the fixture defines a hole, and the method comprises the step of marking an initial insertion location for the first thread of suture material with the hole.

10. The method of claim 1, wherein the first thread of suture material has a leading end and a trailing end, and the method comprises tying the leading end and the trialing end of the first thread in a knot.

11. The method of claim 10, wherein the second thread has a leading end and a trailing end, and the method comprises tying the leading and the trialing end of the second thread in a knot.

12. The method of claim 1, wherein the leaflets are formed from synthetic material.

13. The method of claim 1, wherein the leaflets are formed from animal tissue.

\* \* \* \* \*